US006190382B1

(12) United States Patent
Ormsby et al.

(10) Patent No.: US 6,190,382 B1
(45) Date of Patent: Feb. 20, 2001

(54) RADIO-FREQUENCY BASED CATHETER SYSTEM FOR ABLATION OF BODY TISSUES

(75) Inventors: Theodore C. Ormsby, Milpitas; George L. Leung; Ming-Fan Law, both of San Diego, all of CA (US)

(73) Assignee: Medwaves, Inc.

( * ) Notice: Under 35 U.S.C. 154(b), the term of this patent shall be extended for 0 days.

(21) Appl. No.: 09/211,188

(22) Filed: Dec. 14, 1998

(51) Int. Cl.[7] .................................................. A61B 18/04
(52) U.S. Cl. ................................ 606/33; 606/47; 606/41; 607/101; 607/156; 607/122
(58) Field of Search .................. 606/41, 46, 47, 606/48, 50, 33; 607/101, 119, 122, 156

(56) References Cited

U.S. PATENT DOCUMENTS

| 4,583,556 | | 4/1986 | Hines et al. ........................... 128/804 |
| 5,370,644 | | 12/1994 | Langberg ................. 606/33 |
| 5,545,193 | * | 8/1996 | Fleischman et al. ................... 607/99 |
| 5,683,382 | | 11/1997 | Lenihan et al. ......................... 606/33 |
| 5,702,433 | | 12/1997 | Taylor et al. .......................... 607/101 |
| 5,738,683 | * | 4/1998 | Osypka .................................. 606/47 |
| 5,741,294 | | 4/1998 | Moss et al. .............................. 606/33 |
| 5,755,754 | | 5/1998 | Rudie et al. ........................... 607/101 |
| 5,785,706 | * | 7/1998 | Bednarek ................................ 606/41 |
| 5,800,482 | | 9/1998 | Pameranz et al. .................... 607/101 |
| 5,800,494 | | 9/1998 | Campbell et al. .................... 607/116 |
| 5,837,001 | | 11/1998 | Mackey ................................. 607/102 |
| 5,842,984 | * | 12/1998 | Avitall .................................. 600/374 |
| 5,863,291 | * | 1/1999 | Schaer .................................... 606/41 |
| 5,885,278 | * | 3/1999 | Fleischman ............................ 606/41 |
| 5,971,983 | * | 10/1999 | Lesh ....................................... 606/41 |
| 6,014,579 | * | 1/2000 | Pomeranz et al. ................... 600/374 |
| 6,032,077 | * | 2/2000 | Pomeranz ............................. 607/101 |

* cited by examiner

*Primary Examiner*—Linda S. M. Dvorak
*Assistant Examiner*—David M. Ruddy
(74) *Attorney, Agent, or Firm*—Procopio, Cory, Hargreaves & Savitch, LLP; Kam W. Li

(57) ABSTRACT

An improved radio-frequency catheter system for ablating biological tissues of a body vessel in a patient including a catheter, a deployable antenna guide disposed at the distal portion of the catheter and a radio-frequency ("RF") antenna mounted on the antenna guide. The RF antenna includes a helical coil which defines an axial passageway to accommodate the antenna guide, and is adapted to receive and transmit RF energy for tissue ablation. Upon deployment, the antenna guide acquires a loop configuration which establishes line contact with the body vessel conformable to its internal contour to prescribe the precise and affixed tissue ablation pathway despite body vessel movements. The RF antenna is carried by the antenna guide to be deployed along the established tissue ablation pathway. Alignment of the loop with the desired tissue ablation pathway is facilitated with the use of radio-opaque markers and intracardiac electrodes mounted along the antenna guide. The catheter system is provided with steering mechanism for navigation through the body vessel passageways.

14 Claims, 8 Drawing Sheets

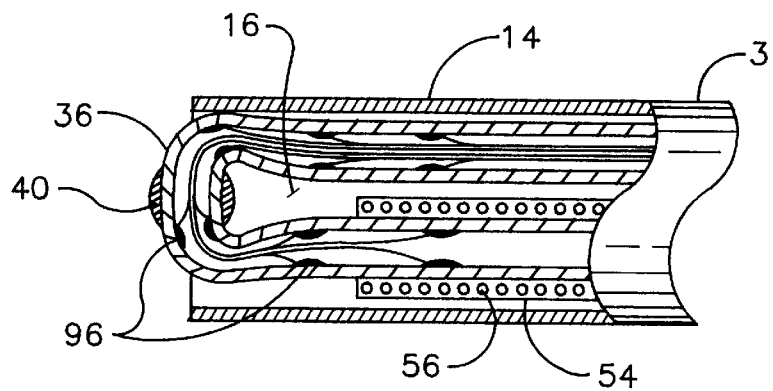
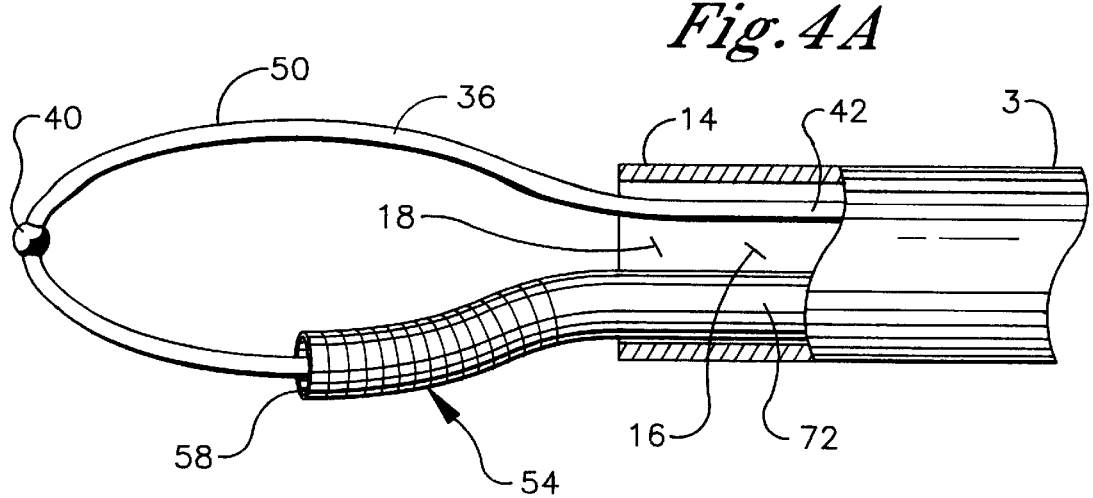

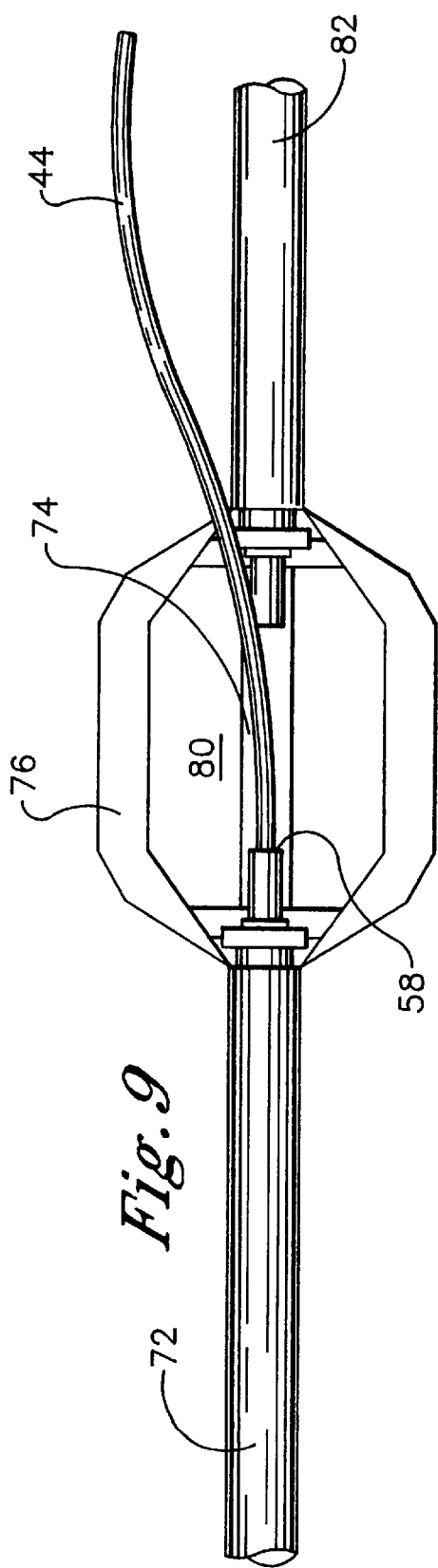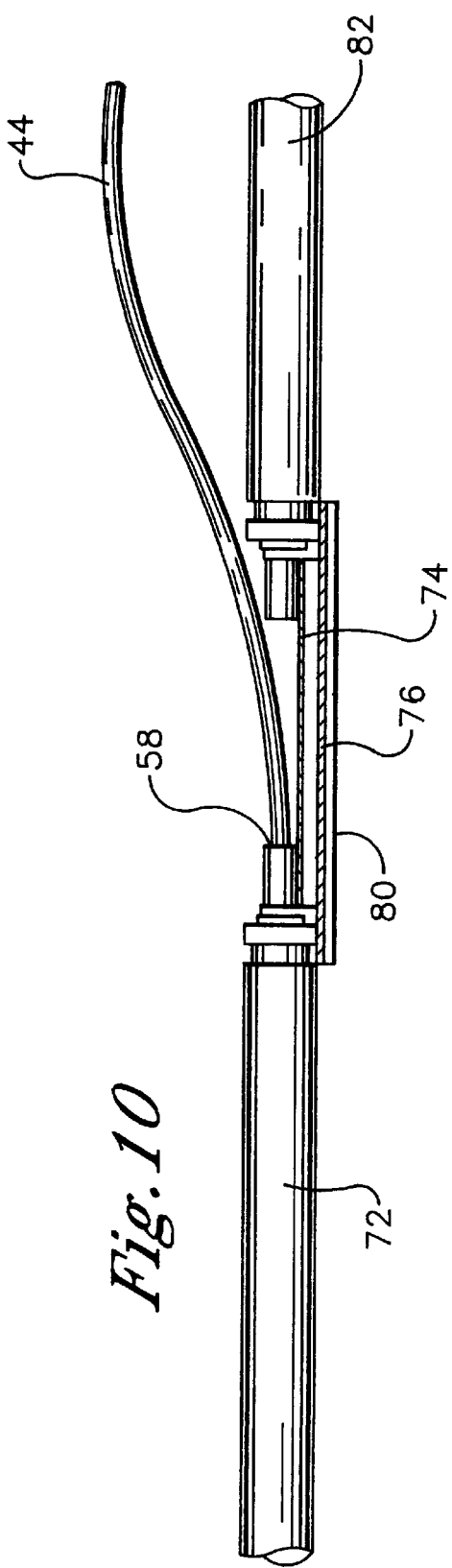

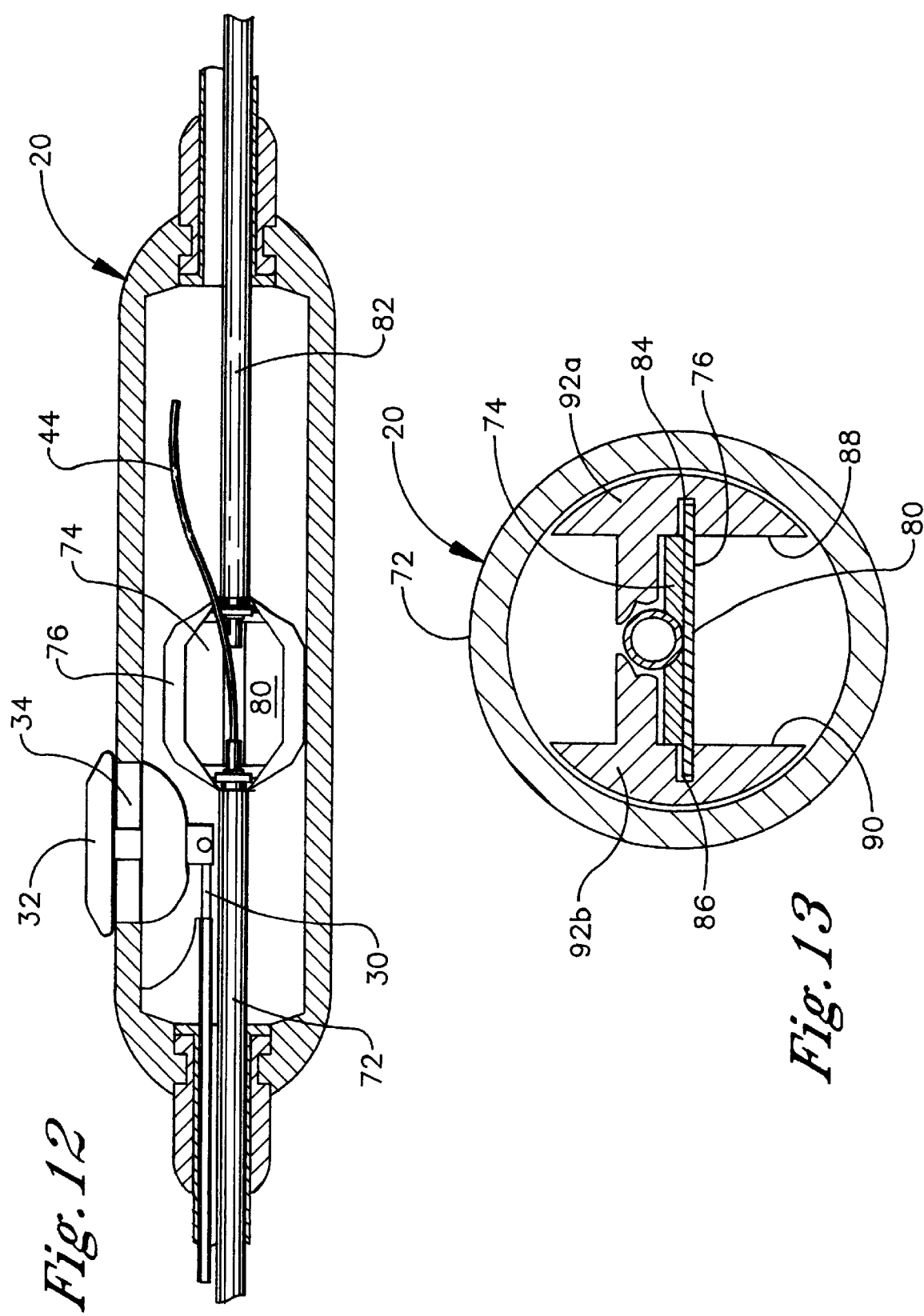

RADIO-FREQUENCY BASED CATHETER SYSTEM FOR ABLATION OF BODY TISSUES

BACKGROUND/FIELD INVENTION

This invention relates generally to radio-frequency ("RF") powered medical apparatus and ablation of biological tissues. More particularly, this invention concerns catheter-based RF antenna for ablating biological tissues within the body vessel of a patient and for the treatment of cardiac arrhythmias.

In recent years medical devices have gained significant acceptance in the medical community as an important treatment modality for heart diseases and other serious ailments, which were traditionally remedied by medication or surgical operation. Two fundamental trends have emerged in the treatment of cardiac diseases. The first has been the shift from open-heart surgical procedures to less invasive and less expensive catheter-based treatments, which are safer and less debilitating.

The second trend is represented by the shift from the use of anti-arrhythmic drugs to minimally invasive catheters or other device-based therapies to palliate incurable arrhythmias. For example, automatic cardioverter-defibrillator are routinely implanted in patients with lethal ventricular arrhythmias to reduce the likelihood of sudden death. Thus, radio-frequency (RF") catheter ablation is now being performed in large number of patients suffering from cardiac arrhythmias.

Despite these advances in technology, atrial fibrillation ("AF") remains a significant challenge. AF, a rapid irregular rhythm in the atria or upper chambers of the heart induced by non-uniformed electrical pulses, represents a leading cause of stroke and heart attack and a major health care burden. To date, the most effective surgical procedure for the treatment of AF has been the Maze procedure undertaken in "open-heart" surgery. In the Maze procedure, incisions are made along pre-determined lines exterior of the atrium, which are then sutured together. As healing develops, scars are formed along the incision lines thereby forming barriers to the conduction of electrical impulses. By creating such barriers, AF can no longer be sustained and regular heart rhythm is restored. However, the Maze procedure has not been widely adopted due to the morbidity and mortality associated with open-heart surgery, which involves the opening of the chest cavity and cutting of the chest bones.

One new approach to mimic the Maze operation is represented by catheter-based radio-frequency ablation technique, wherein, instead of surgical incisions, a catheter-electrode is applied to destroy or ablate the heart tissues inside the atrial chamber. The catheter-electrode is passed through the artery for access to the atrium, as commonly practiced in the medical field. Within the atrium, the tip of the catheter-electrode is positioned, usually with the aid of x-ray or fluoroscopic means, and is brought into contact with the heart tissue at a desired location or spot where ablation is required. At this spot, the tissue is destroyed by resistive heating generated from the catheter-electrode. Thereafter, the catheter-electrode is re-positioned to the next spot for ablation. A series of spot ablations thus mimics the lineal lesions as accomplished under the Maze procedure against the conduction of electrical impulses.

Existing catheter-based ablation procedures are recognizably less intrusive then "open-heart" surgery. In addition, during the ablation, disruption of cardiovascular function is reduced. However, a successful catheter-based radio-frequency ablation procedure requires the ablation of tissue spots within the spatial or proximity tolerance between adjacent spots, usually less than 2 millimeters, to prevent the passage of electrical impulses. In that connection, the task for the precise placement of the catheter-electrode represents a critical element of a successful procedure.

A major drawback of such existing procedures is in the time-consuming task in positioning the catheter-electrode at the desired ablation spots within the atrium while the heart chamber muscles are pulsating. Movements of atrial wall or the heart muscles often render accurate placement of the catheter-electrode difficult, and slippage of the catheter-electrode tends to occur thereby damaging portions of the atrium where ablation is not desired. As a result, placement of the catheter based RF ablation cannot be efficiently accomplished, and prolonged procedure time, in excess of 12 hours, can be expected. Further, during the procedure, x-ray or other irradiating means are routinely employed for locating and positioning the catheter-electrode, which dictates the use of heavy lead protective gear by the electrophysiologist. As a result, such inconvenience is often amplified by the prolonged procedure time, which detracts from the use of catheter-based electrode as an efficient means for tissue ablation.

To minimize the risk of slippage, for example, in U.S. Pat. No. 5,741,249, a catheter-based microwave antenna is disclosed wherein a distal tip is incorporated into the antenna to anchor it to the atrial wall. However, while this design reduces the likelihood of antenna or catheter-electrode slippage during each ablation step, it does not eliminate the consuming task to secure precise placement of the antenna along the desired ablation path for each ablation step. Thus after each ablation step, the antenna has to be re-positioned and anchored precisely at the next spot which must be located within the spatial or proximity tolerance on the ablation path as referenced above.

Accordingly, effective treatments for atrial fibrillation with catheter ablation will require the creation of long or overlapping lineal or curvilineal ablation lesions on the inner surface of the atrium. These lesions can then act as barriers to the conduction of electrical impulses, thus preventing atrial fibrillation.

It is also recognized that a critical requirement for the effective catheter-based ablation of atrial fibrillation is the ability to stabilize and anchor the catheter and microwave antenna inside the atrial chambers. New catheter ablation systems, preferably capable of producing long or overlapping lineal or curvilineal ablation lesions, are required for the development of minimally invasive catheter-based curative procedures for atrial fibrillation.

The present invention provides a design of such a catheter system, which can be used not only for atrial fibrillation but for ablation of biological tissues in other body vessels. The catheter system contains stabilizing and anchoring mechanisms employing monorail and looped antenna guide, sensors for monitoring different parameters during ablation, and handle with control slides for easy steering and manipulation of the catheters.

SUMMARY OF THE INVENTION

According to the present invention, an improved radio-frequency catheter system is provided for ablating biological tissues of a body vessel, including the atrium of a patient. The catheter system comprises a catheter that is adaptable for insertion into the body vessel and a deployable antenna guide disposed within the catheter lumen. A deployable radio-frequency antenna is provided at the distal portion of the catheter to receive and transmit radio-frequency energy for tissue ablation. The antenna includes a helical coil and has an axial passageway to accommodate the antenna guide, which, upon deployment prescribes the ablation pathway of the antenna for tissue ablation. In a representative embodiment of the invention, the antenna guide includes elongated portions which are secured to control slides for positioning and deployment control. The antenna guide is deployable within a body vessel to form a loop configuration that is conformable to the contour of the body vessel. Alignment of the loop with the desired tissue ablation pathway is facilitated with the use of radio-opaque markers and intracardiac electrodes mounted along the antenna guide. After the loop is formed within the body vessel, the radio-frequency antenna will be deployed along the antenna guide for tissue ablation.

In an alternate embodiment of the present invention, one of the elongated portions of the antenna guide is secured to a positioning control slide, and the other portion is secured to the distal portion of the catheter. As a further alternate embodiment of the invention, the antenna guide is formed as an elongated flexible member having a detached distal end portion that is terminated with a distal tip.

In application, the antenna guide is deployed out of the catheter lumen to establish contact with the interior surface of the body vessel. The flexibility of the antenna guide enables it to flex to conform to the contour of the body vessel to form the ablation pathway for the radio-frequency antenna.

The present invention effectively reduces if not avoids the need for repetitive pin-point precision placement of the ablation catheter electrode of the prior art. The present invention conveniently places the radio-frequency antenna along the locus of an antenna guide which defines the tissue ablation pathway. At the same time, the present invention ensures a continuous ablation pathway and substantially reduces the risk of electrical impulse leakage between ablated spots of the prior art. Accordingly, the present invention substantially accomplishes the objective of the Maze procedure in achieving curvilineal lesions yet without the need for open-heart surgery. These and other aspects and advantages of the invention will become apparent from the following detailed description, and the accompanying drawings, which illustrate by way of example the features of the invention.

BRIEF DESCRIPTION OF THE DRAWINGS

FIG. 3B is a sectional view of the antenna guide and the radio-frequency antenna in a retracted position at the distal portion of the radio-frequency catheter ablation system.

FIG. 4A is a partial sectional view of the distal portion of the radio-frequency catheter ablation system.

FIG. 9 is a plan view of a microstrip used for electrical connection between the radio-frequency antenna and a source of the radio-frequency energy.

FIG. 10 is an elevational view of the microstrip of FIG. 9.

FIG. 12 is a partial sectional view of a handle chassis used in the radio-frequency catheter ablation system.

FIG. 13 is a cross-sectional view of the microstrip disposed within the handle chassis of FIG. 12.

DETAILED DESCRIPTION OF THE INVENTION

The current invention provides an improved radio frequency-based catheter system for ablating biological tissues within the body vessel of a patient. The system includes a catheter that is adaptable for insertion into a body vessel of patient. It incorporates a deployable radio-frequency antenna for delivering electromagnetic energy to the treatment site. A monorail guide is provided for precise positioning of the antenna along a desired ablation pathway.

Figure 1:
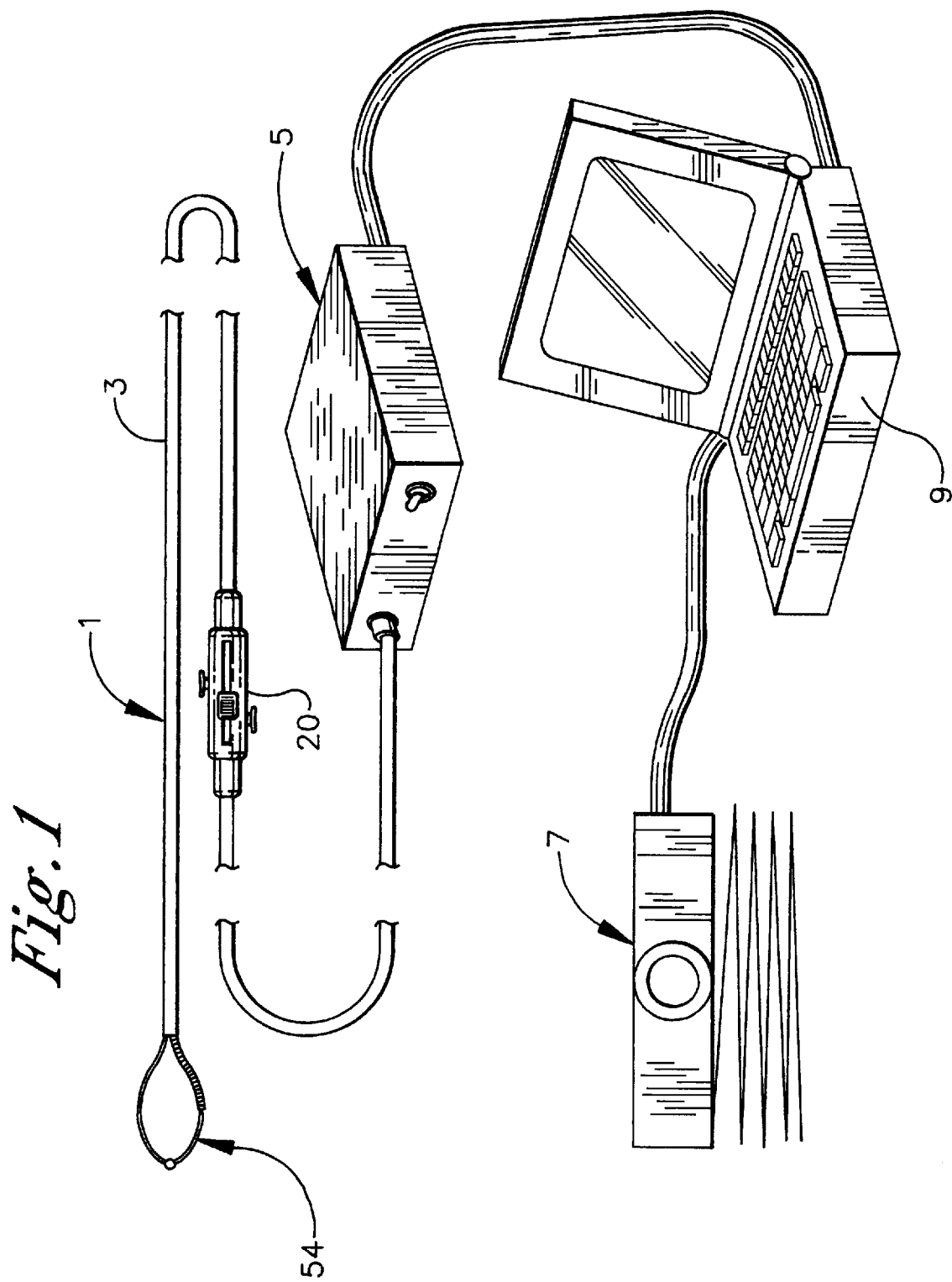
FIG. 1 is a conceptual diagram of a radio-frequency catheter ablation system of the present invention, together with radio-frequency power module, computer control and data recording device.
Figure 2:
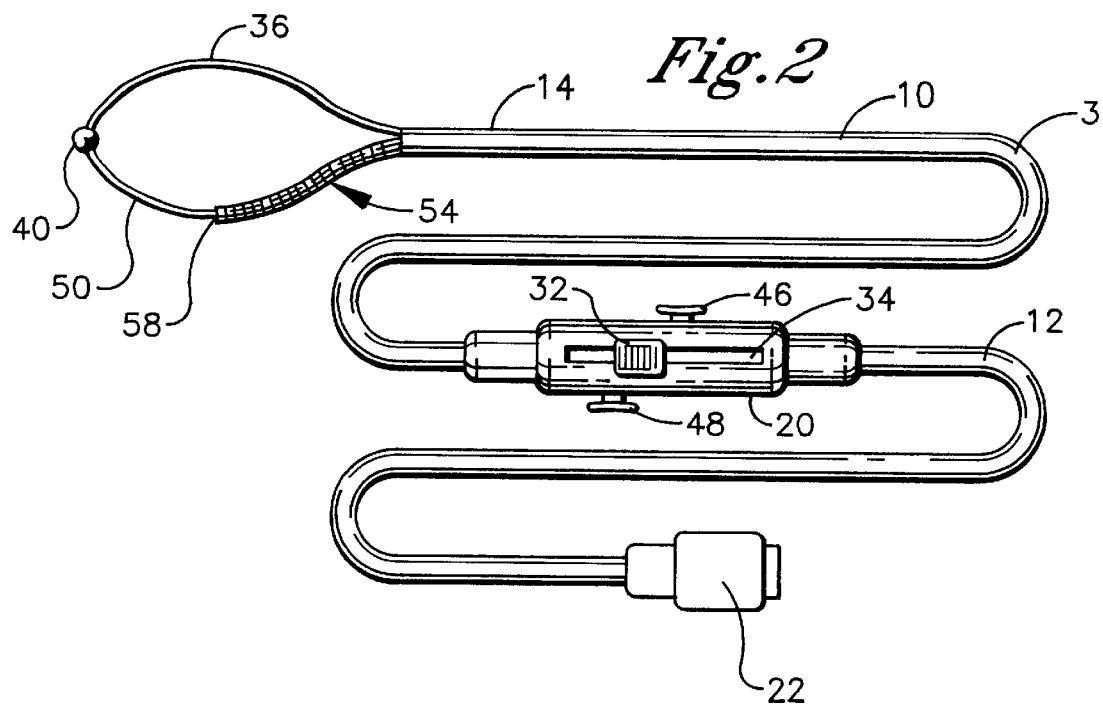
FIG. 2 is a perspective view of the radio-frequency catheter ablation system of the present invention.

As seen in FIGS. 1, 2, and 3, the present invention comprises a catheter 3, which is adapted for insertion into a body vessel of the patient. The catheter has a flexible elongated tubular body 10 with a proximal portion 12 and a distal portion 14. A lumen 16 extends from the proximal portion of the catheter to the distal portion with a distal opening 18 (FIGS. 3 and 4). Located at the proximal portion 12 of catheter 3 is a handle chassis 20 for housing necessary steering and positioning controls, as will be described in further details below. Incorporated at the proximal end of the catheter 3 is a coupling 22 for connecting various electrodes (not shown) in support of the ablation procedure.

The dimensions of catheter 3 are adapted as required to suit the particular medical procedure, which are well known in the medical art. The tubular body 10 of the catheter is generally constructed of polymer materials that are biocompatible within the body vessel environment. Examples of these materials include Pebax from Autochem Germany, polyethylene, polyurethane, polyester, polyimide and polyamide, with varying degrees of radio-pacificity, hardness and elasticity.

In one embodiment of the present invention, the catheter 3 is formed with a plurality of segments using one or more of the afore-mentioned materials such that the catheter body is progressively more flexible toward its distal end. The segments are joined together via thermal bonding, butt joint, or adhesive bonding. Braiding reinforcement can also be added to the circumferential surface of tubular body 10 to attain the desirable level of stiffness and torsional strength for the catheter. This allows the catheter to advance and negotiate through the body vessel of a patient, and to enable torque transfer along the length of the catheter from the proximal portion to the distal portion.

Figure 11:
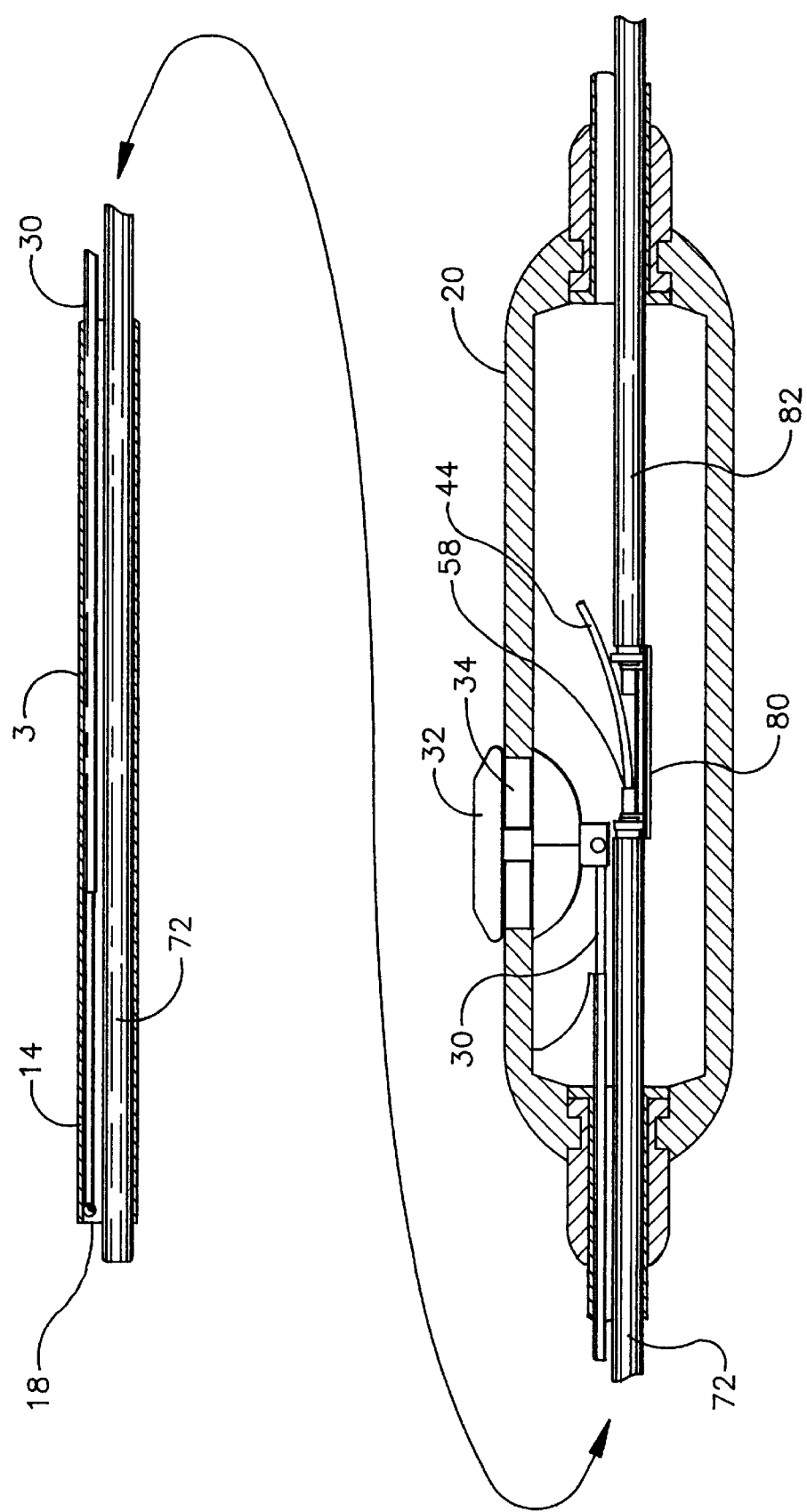
FIG. 11 is a partial sectional view of the radio-frequency catheter ablation system.

The distal portion 14 of catheter 3 consists of a softer polymer compound with little or no braiding to provide the desired flexibility to accommodate distal deflection or steering of the catheter 3 when it is maneuvered through the narrow passageways of body vessels such as arteries or veins. In the present invention, steering of the catheter is implemented by a pull wire 30, which extends from the control handle chassis 20 to the distal portion 14 of the catheter 3, as shown in FIG. 11. At the distal end of catheter 3, pull wire 30 is affixed to the inner wall of the catheter lumen 16 by soldering or other suitable means.

Pull wire 30 is proximally fastened to deflection control grip or thumb slide 32, which is slidably engaged along a longitudinal slot 34 of the handle chassis 20. Longitudinal movement of the thumb slide 32 along slot 34, together with the torsional movement of the catheter 3 enables a physician to bend or straighten the catheter 3 as needed in order to negotiate through the passageways of the body vessel. Incorporated in the thumb slide 32 is frictional capture means for affixing the grip position in the slot 34. Many such means are commercially available. Examples of such means include set-release, pressure switch or self-locking mechanisms.

Figure 3A:
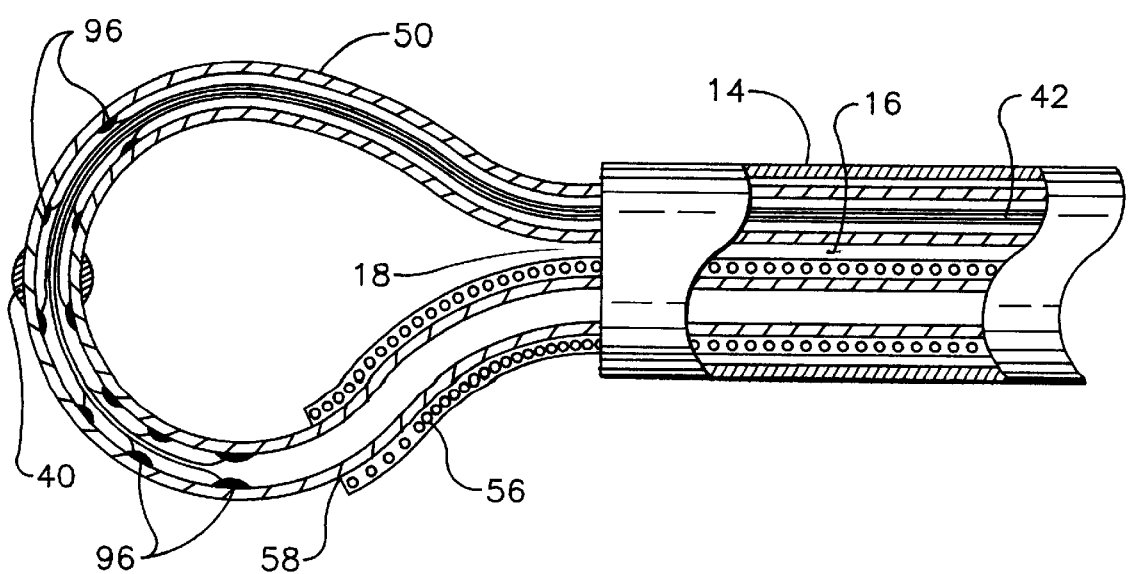
FIG. 3A is a sectional view of the antenna guide and the radio-frequency antenna in a deployed position at the distal portion of the radio-frequency catheter ablation system.

The catheter system 1 of the present invention provides an effective means for guiding a RF antenna for tissue ablation along a predetermined ablation pathway. FIGS. 1, 3A, 4A and 4B show an antenna guide or monorail 36, which is deployed in an extended position adjacent the distal portion 14 of catheter 3. The antenna guide or monorail 36 is also adaptable to be retracted within the catheter lumen 16 as shown in FIG. 3B.

In one embodiment of the present invention, monorail 36 comprises a flexible elongated member, which can be constructed of a strip-like material. Alternatively, monorail 36 can also be made of small-diameter tubing, as shown in the drawings. Monorail 36 has extended portions 42 and 44 which extend proximally within the catheter lumen 16 (FIGS. 4A, 8–10). At the handle chassis 20, monorail extension portions are secured to respective control slides 46 and 48. Similar to the catheter deflection pull wire 30, control slides 46 and 48 are slidably engaged within longitudinal slots on the handle chassis 20, as shown in FIG. 2, and are moveable distally or proximally along the longitudinal axis of the catheter 3. Thus by moving one or both control slides, the monorail guide can establish a deployed position, as shown in FIGS. 2, and 3A, or a retracted position, FIG. 3B. For deployment of the monorail 36, either one or both control slides 46 and 48 are moved distally relative to the handle chassis 20. For retraction, the control slides are moved proximally. The positions of the control slides can be secured with appropriate means such as spring-loaded frictional capture means or the like, as similar to those used for the deflection control or thumb slide 32.

FIG. 3B shows the monorail 36 in a substantially retracted position, where it is arranged in a compact U-shaped fashion within the catheter lumen 16 at the distal portion 14 of the catheter 3. A smooth or curved tip 40 is provided at the monorail 36 such that in the retracted position, tip 40 substantially closes the distal opening 18 of catheter 3 to isolate the catheter lumen 16 from the biological environment. The tip 40 also renders the catheter "atraumatic" and provides a smooth distal profile for the catheter to reduce the risks of body vessel puncture as it is navigated through the passageways of the body vessels.

Tip 40 can be made of bio-compatible materials which are commonly used for the construction of catheters. Further it can incorporate a radio-opaque material to aid in the identification of its location within the body vessel by X-rays or other fluoroscopic means, as commonly practiced in the art.

The monorail 36 is made of materials in either metallic or in the polymer group having appropriate degree of memory, bio-compatibility, and spring-like structural properties. Examples of such materials include nitinol (nickel-titanium), stainless steel, polyamide and polytetrafluroethylene ("PTFE"). Metallic materials used can also be heat treated or cold worked as necessary to provide the desirable structural properties, such as stiffness and flexibility. These structural properties allow monorail 36 to be moved without crinkles within the catheter lumen 16. However, in its deployed position outside the catheter lumen 16, the monorail 36 is adaptable to flex.

Figure 4B:
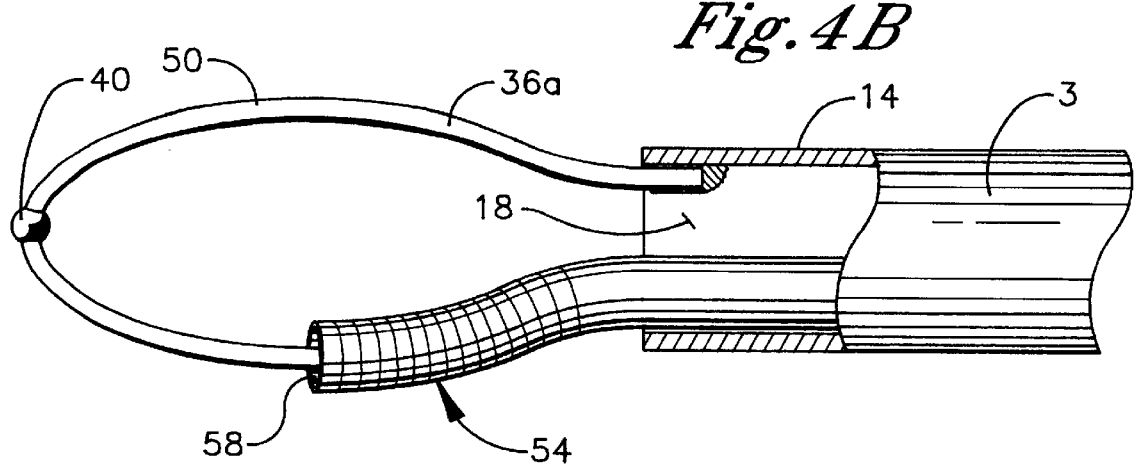
FIG. 4B is a partial sectional view of the distal portion of another embodiment of the radio-frequency catheter ablation system.

Monorail 36 is deployable beyond the distal opening 18 of the catheter 3 within a body vessel to form a substantially continuous loop 50 as shown in FIGS. 3A, 4A and 4B. Monorail deployment is enabled with the longitudinal advancement of control slides 46 and 48 toward the distal end of catheter 3 such that the monorail extends beyond the catheter distal opening 18 to establish contact with the interior wall of the body vessel. Upon such contact, the extended portion of monorail 36 will flex to acquire a loop configuration. Depending on the interior contour the body vessel where treatment is desired, the size of the loop 50 can be adapted by adjusting the amount of distal displacement of the control slides such that the monorail conforms to the contour of the body vessel. The spring-like properties of the monorail 36 make possible that at least a portion of the loop 50 bears against the wall of the body vessel thereby acquiring line contact with the interior wall of the body vessel in spite of its possible movements. The tip 40 further helps in anchoring the monorail 36 at crevices or minor depressions on the interior wall of the body vessel without the risks of causing puncture on the body vessel.

To ascertain the position of the monorail 36 when it is being advanced within a body vessel, one or more radio-opaque markers can be installed on the monorail 36. As shown in FIGS. 1–4, a radio-opaque marker is incorporated into tip 40 of the monorail 36. With the radio-opaque material, tip 40 becomes opaque under x-ray or fluoroscopic examination, thereby aiding the identification of its position during catheter insertion or tissue ablation. The structure and use of radio-opaque markers are well-known in the art, and are not detailed here.

As a variation in design, the antenna guide can be constructed of two separate elongated members joined at the distal tip to form a unitary monorail. The joint angle between the elongated members can be pre-determined based on the profile of the monorail as it is needed for the particular application. Thus by way of example, a low profile (having ultra small cross-section) catheter used in operation within a narrow lumen of a body vessel could require a relatively small joint angle for the elongated members so as to facilitate the monorail retraction and deployment. FIG. 4B shows another embodiment of the present invention, wherein one end of the monorail guide 36a is secured to the catheter 3 adjacent the distal opening 18. The other end of the monorail 36a, which incorporates an extension portion 44a, is attached to a control slide (not shown) at the handle chassis. This embodiment enables the deployment and retraction of the monorail with the use of a single control slide at the handle chassis.

The present invention includes a radio-frequency (RF) antenna 54 disposed adjacent the distal portion 14 of the catheter 3, as shown in FIGS. 2–7, for tissue ablation. The RF antenna 54 includes an electrically conductive material or wire strip that is wound in a helical fashion to form a helical coil 56. The appropriate diameter, pitch and length of the coil winding, and the selection of the conductive material or wire strip are a matter of design choice, which can vary according to the particular procedure requirements as known in the art. Thus these design elements and considerations are not detailed here.

As shown in FIGS. 2, 3 and 4A and 4B, the RF antenna 54 includes the helical coil 56, which defines an axial passageway 58 for accommodating the monorail 36. The RF antenna 54 is slidably mounted over the monorail 36. Thus its movement will be prescribed by the monorail.

To enhance its shape integrity, RF antenna 54 is provided with a tubular liner or sleeve 60, which has a flexible extended body which extends from the helical coil 56 proximally toward the proximal portion 12 of the catheter 3. Sleeve 60 is constructed of a dielectric material, which reduces the likelihood of electrical short between the metallic surfaces of helical coil 56 and body fluids in the passageway 58, and to help confine the electro-magnetic field to the outside of the passageway.

Figure 5:
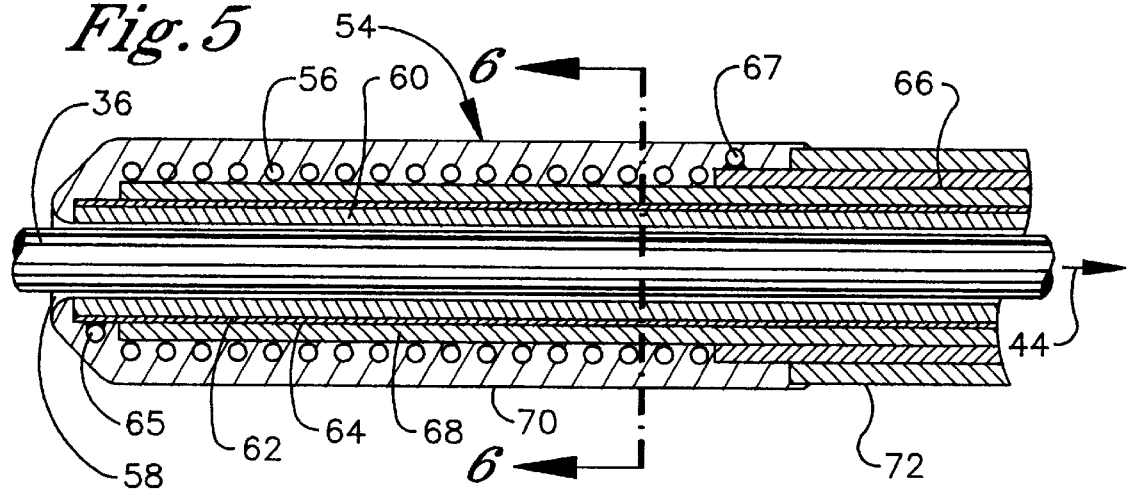
FIG. 5 is sectional view of the radio-frequency antenna and a partial view of the antenna guide.
Figure 6:
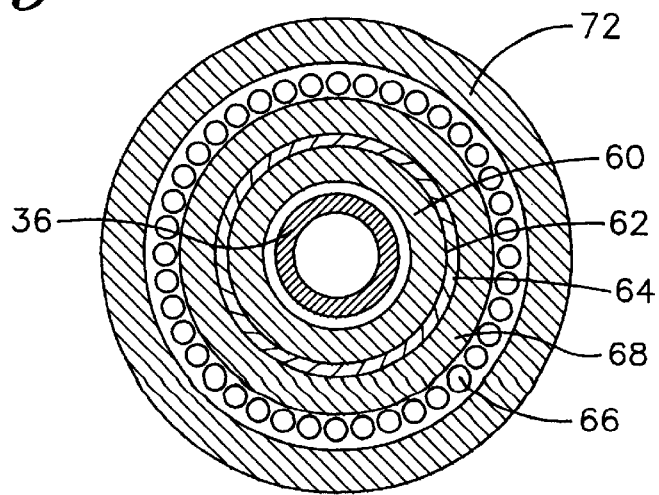
FIG. 6 is a cross-sectional view taken from line 6—6 of FIG. 5.

As shown in FIGS. 5 and 6, helical coil 56 is coupled at contact points 65 to a first or inner electrical conductor 64, which is in turn electrically coupled to a source of RF energy provided by the RF power control source 5. In the embodiment shown in FIGS. 5, 6 and 11, inner conductor 64 is made of a flexible braided wired construction or thin film electrically conductive material, which circumscribes the outer surface 62 of sleeve 60 and extends proximally from the helical coil 56 to the handle chassis 20. In this embodiment, inner conductor 64 assumes an elongated tubular configuration.

Inner conductor 64 is coated with a polymeric dielectric protective coating 68 along its outer circumferential surface and extends proximally to the handle chassis. Protective coating 68 serves as a substrate for the helical coil 56 and for a second or outer conductor 66. Protective coating electrically isolates the inner conductor 64 from the outer conductor 66.

As shown in FIGS. 5 and 6, helical coil 56 is wound around the outer circumferential surface of the protective coating 68 and is connected to outer conductor 66 at contact point 67. In turn, outer conductor 66 is electrically coupled to the source of RF energy provided by the RF power control source 5.

In the embodiment as shown in FIGS. 5 and 6, outer conductor 66 is made of an electrically conductive material circumscribing the dielectric protective coating 68, and extends from the helical coil 56 proximally toward the handle chassis 20. The outer conductor can be made of braided wired construction or thin film electrically conductive material.

As shown in FIG. 5, the helical coil 56 is coated with a polymeric dielectric encapsulant 70 along its outer circumferential surface to ensure the structural integrity of the helical coil and to protect same from the biological environment. Encapsulant 70 is made of suitable materials such as silicon or polymer-based materials or rubber compounds. Similarly, an outer jacket 72 made of similar materials is provided to encase the outer conductor 66 and to provide electromagnetic and thermal isolation from the biological environment.

As shown in FIG. 11, outer jacket 72 is coupled to a microstrip 80, which is slidably secured to the handle chassis 20 for the axial displacement of the RF antenna at the proximal portion, as will be discussed in more details below. The extended portion 44 of monorail 36 extends proximally within the passageway 58 to the proximal portion 12 of the catheter 3. Thus the present invention provides for a set of electrical conductors each of which is formed in an elongated tubular configuration and arranged in a substantially coaxially aligned relationship with each other to form a hollow cable which extends from the helical coil 56 proximally to the handle chassis 20 for the delivery of RF energy.

The RF antenna 54 is adapted to receive and radiate electromagnetic energy from a source of radio-frequency energy (not shown). An example of suitable spectrum of radio frequency is that of the microwave frequency ranging from approximately 300 mHz and up. The RF antenna is capable of applying substantially uniformly distributed electromagnetic field energy transmitted by the helical coil. The power of the electromagnetic field transmitted is substantially normal to the longitudinal axis of the RF antenna, and therefore producing uniform energy field circularly about and bounded by the antenna. The energy delivered for the ablation will be uniformly distributed along the antenna, which is independent of the contact between the antenna and the tissue to be ablated. As a result, the present invention reduces the likelihood of creating hot spots in tissue and blood in close proximity or in contact during ablation in comparison to the spot conductive or resistive ablation catheter of the prior art.

At the handle chassis 20, the inner conductor 64 and outer conductor 66 are terminated with coupling to respective junction plates 74 and 76 of an impedance matching microstrip 80 (FIGS. 11–13). Junction plates in turn are coupled to an electrical conductor 82, for example solid co-axial cable, which extends from the handle chassis 20 to a source of electromagnetic energy (not shown) via wire connector 22. At the microstrip, monorail 36 exits the sleeve 60 of the RF antenna, which enables it to be connected to one of control slides.

Microstrip 80 is slidably engaged along the side channels 84 and 86 on the opposite side walls 88 and 90 of a mounting blocks 92a and 92b housed with the handle chassis 20. To provide for the axial movement of the RF antenna, cable 82 can be moved distally or proximally relative to the handle chassis for the deployment or retraction of the RF antenna. Alternatively, microstrip 80 can be secured to a positioning slide which is moveable along a longitudinal slot on the handle chassis 20 (not shown).

Proper placement of the guide member is aided by the radio-opaque marker 40 as discussed above. In addition, monorail 36 can be provided with one or more intracardiac electrocardiogram ("ECG") electrodes 96 for the physicians to obtain both optimum tissue proximity and electrical conductive activities before and after tissue ablation, as well as to obtain feedback of their actions. These electrodes are secured along the length of the monorail 36. FIG. 3A shows a typical arrangement of intracardiac electrodes 96, which are electrically coupled to conductors disposed within the monorail 36 to terminate into the signal pins (not shown) provided for in the wire connector 22.

The catheter is adaptable to be inserted through an opening into a body vessel of a patient where it is brought into the proximity of target tissue for ablation. Prior to the insertion, both the guide member 36 and the RF antenna 54 are retracted within the catheter lumen 16 with the radio-opaque marker 40 to attain an atraumatic tip configuration for the catheter to facilitate smooth passage. The distal portion 14 of the catheter 3 is then inserted into the body opening and is manipulated to reach within the proximity of the location where ablation is needed. Directional control is accomplished with rotational action on the handle chassis and the use of the deflection control 32.

Placement of the RF antenna guide member or monorail 36 is facilitated by the radio-opaque marker 40, whose position can be detected by suitable x-ray or fluoroscopic means, as practiced in the art. After the distal portion 14 of the catheter 3 is placed within the proximity of the tissue ablation site, the monorail is moved distally by the control slides so it exits the catheter lumen opening 16 to acquire an extended or a deployed position loop configuration as described above.

Depending on the internal shape and dimensions of the body vessel, one or both of the monorail control slides can be manipulated to acquire the desired monorail loop size or profile. Acquisition of the loop size or profile is further aided with the use of the intracardiac ECG electrodes 96 for the physician to align the RF antenna guide or monorail 36 with the desired ablation pathway.

By way of example, in the case of an atrium of the heart, the size of loop 50 can be adjusted to conform to the is contour of the interior wall of the atrium to allow at least a portion of the loop 50 to rest upon the atrial wall, which establishes line contact between the atrium and the monorail. The flexibility of the monorail 36 allows at least a portion of the loop to conform to the internal contour of body vessel and to rest against its internal wall. As the atrial wall pulsates, the monorail, which is in contact with the atrial wall, will also move in concert, thereby achieving an affixed and stable relationship with the location of the body vessel where treatment is desired.

Once the loop profile for the monorail has been acquired and aligned in parallel with the desired ablation pathway, the control slides 46 and 48 are secured in position at the handle control. The RF antenna 54 is then moved distally to exit the distal end opening of the catheter and slidably guided by the monorail to reach the precise location where ablation is needed. Thereafter, tissue ablation can be accomplished with the application of radio-frequency energy. Depending on the particular procedure requirements, the length of the ablation can be adjusted by positioning the RF antenna along various locations along the loop followed by applications of the RF energy. Thus, long and contiguous ablation lines can be established to substantially eliminate the risk of electrical impulse leakage between ablated tissue pathways. The above steps can be repeated for other locations within the atrium as necessary depending on the particular procedure requirements.

Figure 7:
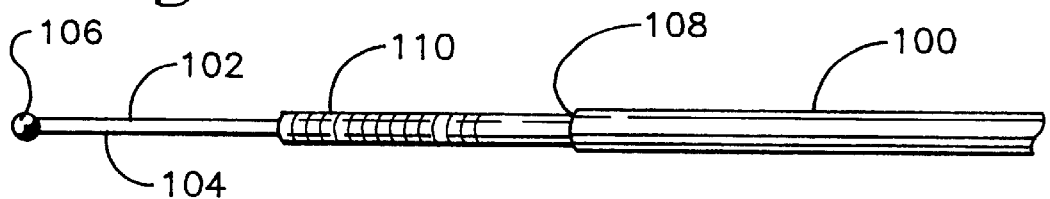
FIG. 7 is a perspective view of another embodiment of the present invention.
Figure 8:
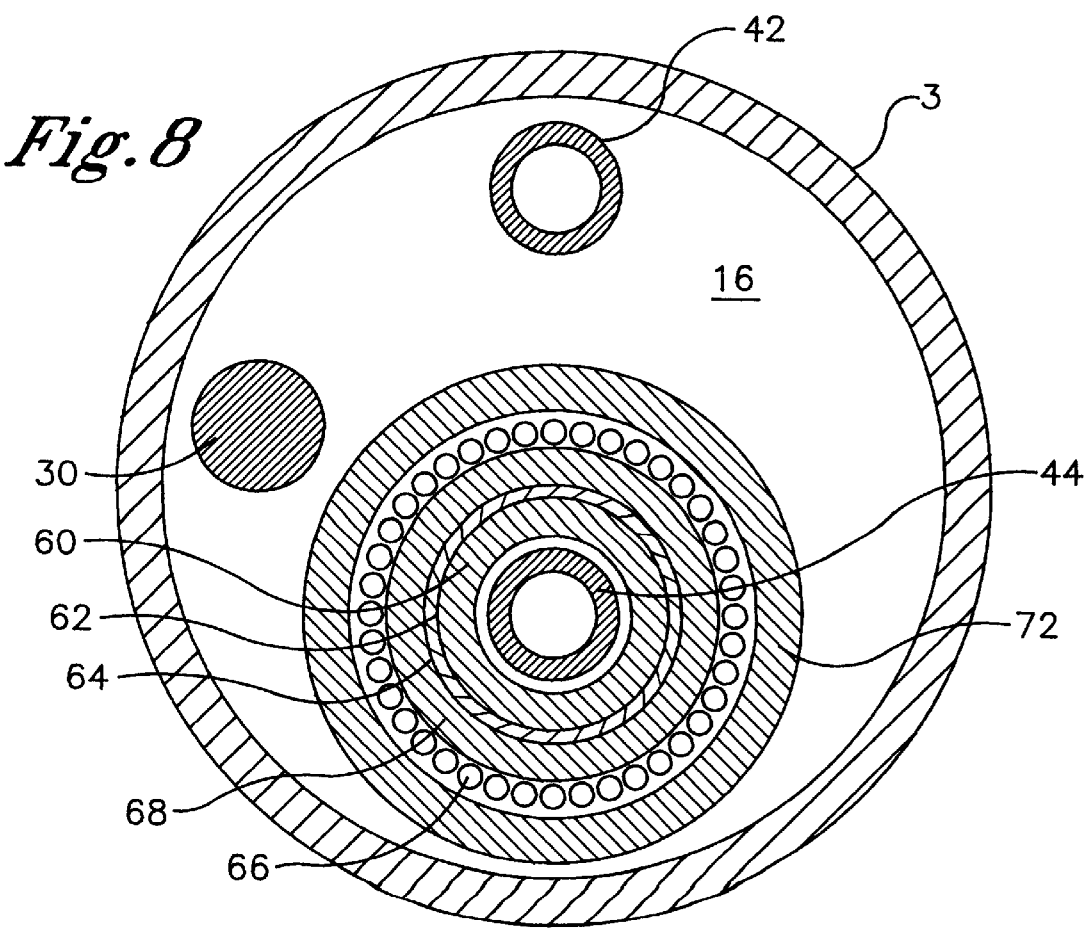
FIG. 8 is a typical cross-sectional view of distal portion of the catheter system.

FIG. 7 shows another embodiment of the present invention which incorporates a variation of the antenna guide design. In this embodiment, the antenna guide 102 comprises an elongated flexible member having a detached distal end portion 104 that is terminated with a distal tip 106. The distal tip 106 is incorporated with a radio-opaque material to aid in the placement of the catheter as described above. The other end portion of the guide 102 extends proximally to a handle chassis (not shown) and is secured to a positioning control slide (not shown) in a similar fashion as the embodiments described above. Similarly, the antenna guide 102 can be retracted within the lumen of the catheter 100 prior to its deployment, together with a RF antenna 110.

In application, after the catheter 100 is placed within the proximity of the tissue to be ablated, the antenna guide 102 is deployed out of the catheter lumen 108 where the distal tip 106 is allowed to anchor within crevices on the surface of the body vessel. The flexibility of the antenna guide 102 enables it to flex to conform to the contour of the body vessel and establishes line contact between the guide 102 and the body vessel. Thereafter, the RF antenna 110 is carried by the antenna guide 102 to be extended out of the catheter lumen 108 for the ablation along a pathway that is substantially aligned in parallel with the line contact between the antenna guide 102 and the body vessel.

From the above description, it is apparent that the present invention effectively reduces if not eliminates the need for repetitive pin-point precision placement of the ablation catheter electrodes of the prior art. The present invention conveniently places the RF antenna along the locus of an antenna guide which defines the tissue ablation pathway. At the same time, the present invention ensures a continuous ablation pathway and substantially reduces the risk of electrical impulse leakage between ablated spots of the prior art. Accordingly, the present invention substantially accomplishes the objective of the Maze procedure in achieving lineal lesions yet without the need for open-heart surgery.

While the above description of the invention is directed to the present embodiments or examples of applications, various modifications and improvements can be made without departing from the spirit and scope of the invention.

What is claimed is:

1. A radio-frequency-based catheter system for ablating biological tissues within the body vessel of a patient comprising:

(a) a catheter adapted for insertion into the body vessel of the patient, the catheter having a proximal portion, a distal portion with an distal opening and a lumen extending from the proximal portion to the distal portion;

(b) an elongated antenna guide disposed within the catheter lumen and deployable beyond the distal opening of the catheter to form a loop substantially conformable to the internal contour of the body vessel;

(c) a radio-frequency antenna disposed at the distal portion of the catheter, the antenna including a helical coil and defining an axial passageway to accommodate the antenna guide passing therethrough, the radio-frequency antenna being adaptable to receive and irradiate radio-frequency energy for ablating the biological tissues along a biological ablation pathway; and (d) an electrical conductor coupled to each end of the helical coil and extending proximally toward the proximal portion of the catheter within the lumen wherein the electrical conductors are adapted to transmit radio-frequency energy at a frequency greater than 300 Megahertz (MHz) of the electromagnetic spectrum.

2. The catheter system according to claim 1, wherein the radio-frequency antenna further comprises a tubular liner circumscribed by the helical coil and defining the axial passageway.

3. The catheter system according to claim 1, wherein at least one of the electrical conductors is formed of an elongated tubular material.

4. The catheter system according to claim 1, wherein the electrical conductors are each formed of an elongated tubular material and arranged in a substantially coaxially aligned relationship with each other to form a hollow cable defining a passageway to accommodate the antenna guide passing therethrough.

5. The catheter system according to claim 1, wherein at least one of the electrical conductors is formed of a braided electrically conductive material.

6. The catheter system according to claim 1, wherein the antenna guide has extended portions extending proximally within the catheter lumen.

7. The catheter system according to claim 1, wherein the antenna guide is constructed of tubing material.

8. The catheter system according to claim 7 which further comprises at least one intracardiac electrocardiogram electrodes mounted within the antenna guide.

9. The catheter system according to claim 1, wherein the antenna guide is constructed of a plurality of elongated members joined to form a unitary monorail.

10. The catheter system according to claim 1 wherein the antenna guide further comprises at least one distal tip formed of radio-opaque material.

11. A radio-frequency-based catheter system for ablating biological tissues within the body vessel of a patient comprising:
   (a) a catheter adapted for insertion into the body vessel of the patient, the catheter having a proximal portion, a distal portion with an distal opening and a lumen extending from the proximal portion to the distal portion;
   (b) an elongated antenna guide slidably disposed within the catheter lumen and having a first end portion secured to the distal portion of the catheter and a second end portion extending proximally within the catheter lumen, the antenna guide being deployable beyond the distal opening of the catheter to form a loop having a portion conformable to the interior contour of the body vessel;
   (c) a radio-frequency antenna disposed at the distal portion of the catheter, the antenna including a helical coil and defining an axial passageway to accommodate the antenna guide passing therethrough, the radio-frequency antenna being adaptable to receive and irradiate radio-frequency energy for ablating the biological tissues along a biological ablation pathway; and
   (d) an electrical conductor coupled to each end of the helical coil and extending proximally toward the proximal portion of the catheter within the lumen wherein the electrical conductors are adapted to transmit radio-frequency energy at a frequency greater than 300 Megahertz (MHz) in the electromagnetic spectrum.

12. A radio-frequency-based catheter system for ablating biological tissues within the body vessel of a patient comprising:
   (a) a catheter adapted for insertion into the body vessel of the patient, the catheter having a proximal portion, a distal portion with a distal opening and a lumen extending from the proximal portion to the distal portion;
   (b) an elongated flexible antenna guide slidably disposed within the catheter lumen and deployable beyond the distal opening of the catheter forming line contact with the body vessel and substantially conforming to the contour of the body vessel to define a biological ablation pathway;
   (c) a radio-frequency antenna disposed at the distal portion of the catheter, the antenna including a helical coil and defining an axial passageway to accommodate the antenna guide passing therethrough, the radio-frequency antenna being adaptable to receive and transmit radio-frequency energy for ablating the biological tissues along the ablation pathway; and
   (d) an electrical conductor coupled to each end of the helical coil and extending proximally toward the proximal portion of the catheter within the lumen wherein the electrical conductors are adapted to transmit radio-frequency energy at a frequency greater than 300 MHz in the electromagnetic spectrum.

13. The catheter system according to claim 12 wherein the antenna guide further comprises at least one distal tip formed of radio-opaque material.

14. The catheter system according to claim 12 wherein the antenna guide is constructed of tubular material.

* * * * *